United States Patent [19]
Block, Jr.

[11] Patent Number: 5,830,185
[45] Date of Patent: Nov. 3, 1998

[54] POSITION-INDEPENDENT FLUID TRAP

[75] Inventor: Frank E. Block, Jr., Little Rock, Ark.

[73] Assignee: Instrumentarium Corp., Finland

[21] Appl. No.: 542,424

[22] Filed: Oct. 12, 1995

[51] Int. Cl.⁶ .................................................. A61M 1/00
[52] U.S. Cl. ...................... 604/122; 128/205.12
[58] Field of Search ...................... 128/205.12; 604/122; 95/260; 96/205, 220; 210/112, 175, 180, 181, 188

[56] References Cited

U.S. PATENT DOCUMENTS

| | | | |
|---|---|---|---|
| 2,002,008 | 5/1935 | Harris, Jr. | 604/122 |
| 3,042,038 | 7/1962 | Beacham | 128/214 |
| 3,533,400 | 10/1970 | Palich | 128/205 |
| 3,793,805 | 2/1974 | Hoffman | 95/260 |
| 3,834,386 | 9/1974 | Sisley | 128/214 |
| 3,926,594 | 12/1975 | Seib et al. | 96/220 |
| 3,938,539 | 2/1976 | Strouth et al. | 137/202 |
| 3,964,479 | 6/1976 | Boag et al. | 128/214 |
| 3,976,068 | 8/1976 | Lindquist | 128/214 |
| 4,061,031 | 12/1977 | Grimsrud | 96/220 |
| 4,175,558 | 11/1979 | Hess, III et al. | 128/214 |
| 4,197,858 | 4/1980 | Osborn | 128/778 |
| 4,198,971 | 4/1980 | Noiles | 128/214 |
| 4,304,578 | 12/1981 | Hakala et al. | 55/189 |
| 4,382,806 | 5/1983 | Hakala et al. | 55/18 |
| 4,504,396 | 3/1985 | Vardi et al. | 95/260 |
| 4,559,034 | 12/1985 | Kirita et al. | 604/52 |
| 4,586,925 | 5/1986 | Carlsson et al | 604/251 |
| 4,636,196 | 1/1987 | Tsuji et al. | 604/122 |
| 4,643,713 | 2/1987 | Viitala | 604/122 |
| 4,678,460 | 7/1987 | Rosner | 604/113 |
| 4,687,495 | 8/1987 | Maddox | 95/260 |
| 4,799,374 | 1/1989 | Bossart et al. | 73/1 |
| 4,886,528 | 12/1989 | Aaltonen et al. | 55/158 |
| 4,964,984 | 10/1990 | Reeder et al. | 96/220 |
| 4,976,685 | 12/1990 | Block, Jr. | 604/122 |
| 4,985,055 | 1/1991 | Thorne, et al. | 128/205.12 |
| 5,394,881 | 3/1995 | Block, Jr. | 128/716 |
| 5,507,858 | 4/1996 | Jepson | 96/220 |
| 5,651,765 | 7/1997 | Haworth et al. | 210/188 |

*Primary Examiner*—Aaron J. Lewis
*Attorney, Agent, or Firm*—Mueller and Smith

[57] ABSTRACT

A position-independent fluid trap for separating at least a portion of a first fluid of a first density entrained within a flow stream of a second fluid of a second density flowing through a fluid circuit. The trap is connectable within the fluid circuit to a first length of tubing defining an inlet line and to a second length of tubing defining an outlet line, and includes a housing enclosing an interior chamber having a geometric extent of a given volumetric capacity. An inlet port is provided to open in fluid communication with the interior chamber and to be couplable to the inlet line. An outlet tube is provided to extend from a proximal end couplable to the outlet line to a distal end disposed within the housing and opening in fluid communication with the interior chamber. Within the interior chamber, the first and second fluid are separated at an interface into a first and second fluid component according to the relative densities thereof. The outlet line distal end is disposed within the chamber effective to define with respect to the interface a predetermined fill volume of the second fluid maintaining the outlet line distal end within the second fluid component. This fill volume is substantially independent of the orientation of the trap within the fluid circuit.

34 Claims, 5 Drawing Sheets

POSITION-INDEPENDENT FLUID TRAP

BACKGROUND OF THE INVENTION

The present invention is directed to a fluid trap or separator which may be adapted for use within an extracorporeal fluid line of a patient, and which effects a fluid fill level substantially independently of the position or orientation of the trap.

Fluid traps are commonly utilized in the extracorporeal fluid circuits of patients undergoing circulatory management. As is detailed by Block, Jr., U.S. Pat. No. 4,976,685, fluid traps are employed within hemodynamic or other fluid circuits used for the intravenous delivery of blood or other fluids. Such circuits typically comprise an arrangement of tubing, filters, and access ports for effecting the infusion of blood or the like to the patient, typically via a hydrostatic pressure transport mechanism. As the blood being supplied to the patient typically is stored at a temperature of about 4° C., it must be normalized to about body temperature within the fluid circuit to avoid a transfusion induced hypothermic response. Such a response has been observed to produce various complications including a decreased cardiac output, and arrhythmias.

For warming the blood being delivered, heat exchangers have been incorporated into the fluid circuit. Exemplary of such heat exchangers are devices such as those manufactured by the Dupaco Company under the name HEMOKINETOTHERM™, which employ a heated water bath to warm the blood or other fluid as it is circulated through a coiled length of tubing. Other exchangers, such as the HOTLINE™ warmer manufactured by Level 1 Technologies, Inc., of Rockland, Mass., employs a concentric tube arrangement wherein the fluid being warmed flows through a central tube about which is circulated heated water flowing through an outer tube. Another exchanger manufactured by Baxter Healthcare Corp. utilizes a series of baffles through which the blood is circulated. U.S. Pat. No. 4,678, 460 discloses a heat exchanger for the rapid infusion and warming of parenteral fluids during trauma, surgery, and other situations of blood loss.

Although heated water is commonly used as the heat transfer medium, radiant or conductive "dry" heat transfer mechanisms also are used. Common to all of the warming devices, however, is a capability for heating the blood or other fluid to a temperature of about 35°–40° C. in a manner which does not destroy the protein and cells which are carried within the fluid.

The warming of the blood or other fluid from its storage temperature to about body temperature does decrease the solubility of the gases dissolved therein to a point where significant outgassing occurs. Attendant with this outgassing is the formation of air or other gas bubbles which, without intervention, would be infused into the patient along with the fluid being administered. In a condition referred to as an air embolism, the infused air or other gas may develop as an embolus which is venously passed from the right ventricle of the heart to the lungs. The embolus increases the pressure in the pulmonary artery, leading to pulmonary hypertension, and also impairs the exchange of oxygen and carbon dioxide across the lungs. Indeed, a sufficiently large air embolus may prove fatal.

For removing the air which has been outgassed during the warming of the blood, the aforementioned fluid traps are incorporated into the hemodynamic circuit intermediate the warmer and the patient. In basic construction, as exemplified by Block in U.S. Pat. No. 4,976,685, and by others in U.S. Pat. Nos. 3,042,038; 3,533,400; 3,834,386; 3,964,479; 3,976,068; 3,938,539; 4,175,558; 4,198,971; 4,559,034; and 4,586,925; such traps typically involve a cylindrical drip chamber which is configured for a generally upright disposition as having an upper entrance port connected to an inlet line, and a lower exit port connected to an outlet line. As the blood or other parenteral liquid is delivered hydrostatically or by pressure infusion, the air or other gas component which is outgassed as the fluid is warmed in the warmer is accumulated within the drip chamber. The liquid component collects in the bottom of the chamber for delivery to the patient via the outlet line. However, if the trap should happen to be inverted or otherwise disturbed from a generally upright disposition, the sequence of the gas-liquid interface developed in the chamber may be reversed such that the gas or air being accumulated may be unintentionally infused into the patient.

Fluid circuits additionally are utilized in the respiratory management of ventilator patients. In intensive care unit (ICU), operating room (OR), and even home settings, mechanical ventilation is provided to effect inspiratory and expiratory control of patients exhibiting acute or chronic respiratory aliments, or undergoing anesthesia. Such patients typically are intubated with endotracheal (ET) tubes which are inserted nasally, orally, or through a tracheostomy opening to deliver respiratory gases directly to the trachea. Somewhat less commonly employed are other respiratory circuits such as laryngeal mask airways.

Generally common to all these circuits, however, is that the inspired gas delivered to the patient is often heated and/or humidified. The relatively high humidity of the inspired air may develop condensation in the tubing circuitry which, for the most part, is an unsatisfactory condition. Moreover, the airway of the intubated patient typically is saturated with water vapor, and often additionally contains mucous or other secretions which also collects in the tubing. These secretions may require frequent suctioning sometimes via a "closed suction" procedure which is relatively complex because of the need in may cases to maintain a positive airway pressure from the ventilator and prevent the lungs of the patient from collapsing during suctioning. Often, the secretions simply are moved up and down the ET tube by the coughing of the patient until the next suctioning.

Rather than merely presenting an unsatisfactory condition in the airway tubing, the condensates and secretions may enter a sampling port which is provided for airway sampling by a gas monitor. As is detailed again by Block in U.S. Pat. No. 5,394,881, gas monitors are used to measure a patient's inspiratory or expiratory gases. However, any liquid such as the condensates and secretions in the airway tubing may temporarily or even permanently damage the sensor or detector mechanisms of the gas analyzer. For example, liquid entering an infrared analyzer chamber inevitably will attenuate the radiation and give rise to spurious readings. Consequently, the chamber must be cleaned or replaced if contaminated with fluid.

Liquid traps or separators for use within the sampling tubing leading to the gas analyzer are disclosed in U.S. Pat. Nos. 4,197,858; 4,304,578; 4,382,806; 4,799,374; and 4,886,528. Generally typical of such traps, as well as the traps for use in circulatory circuits, is a position sensitivity which necessitates the disposition of the trap in a particular orientation to insure its proper operation. Many fluid circuits, however, including the types described herein, preclude the mounting or other positioning of the trap in a fixed orientation. Thus, the traps are prone to tipping or the like which presents a definite risk of a gas embolus or liquid bolus being delivered to the patient. It therefore will be appreciated that improved fluid traps for respiratory, circulatory, and like fluid circuits would be well-received by health care providers, and would represent an important advance in patient care.

BROAD STATEMENT OF THE INVENTION

The present invention is addressed to a position-independent fluid trap adapted for accumulating or otherwise separating a first fluid entrained within a flow stream of a second fluid. The first and second fluids may be, independently, a liquid such as blood, water, mucous, sputum, or other secretion, or a gas such as air or respiratory gas. In a specific application, the trap of the present invention may be used for separating at least a portion of a first fluid of a first density entrained within a flow stream of a second fluid of a second density flowing through an extracorporeal fluid circuit of a patient. The trap is connectable within respiratory, circulatory, or like fluid circuits of a patient which heretofore have not been amenable to the positioning of a fluid trap except in an upright or other fixed orientation. Importantly, the trap is configured as having an outlet tube which extends within a housing of the trap to open in fluid communication with an interior chamber thereof. Once accumulated within the interior chamber of the trap, the first and second fluids are separated at an interface into a first and second fluid component according to the relative densities thereof. In this regard, the outlet line distal end is disposed within the interior chamber effective to define with respect to the interface a predetermined fill volume of the second fluid maintaining the outlet line distal end within the second fluid component. Such predetermined fill level, advantageously, is substantially independent of the orientation of the trap within the fluid circuit. Thus, as the trap is rotated or otherwise positioned to affect the orientation or level of the fluid interface developed within the interior chamber, the distal end of the outlet is maintained within the level of the second fluid for the delivery of that fluid through the outlet line.

It is therefore a feature of the invention to provide a position-independent fluid trap for separating at least a portion of a first fluid of a first density entrained within a flow stream of a second fluid of a second density flowing through a fluid circuit. The trap is connectable within the fluid circuit to a first conduit defining an inlet line and to a second conduit defining an outlet line, and includes a housing enclosing an interior chamber having a geometric extent of a given volumetric capacity. An inlet port is provided to open in fluid communication with the interior chamber and to be couplable to the inlet line. An outlet tube is provided to extend from a proximal end couplable to the outlet line to a distal end disposed within the housing and opening in fluid communication with the interior chamber. Within the interior chamber, the first and second fluid are separated at an interface into a first and second fluid component according to the relative densities thereof. The outlet line distal end is disposed within the chamber effective to define with respect to the interface a predetermined fill volume of the second fluid maintaining the outlet line distal end within the second fluid component. This fill volume is substantially independent of the orientation of the trap within the fluid circuit.

It is a further feature of the present invention to provide a method within a fluid circuit for separating at least a portion of a first fluid of a first density entrained within a flow stream of a second fluid of a second density. A fluid trap is provided within the fluid circuit as connected to a first conduit defining an inlet line of the trap and to a second conduit defining an outlet line of the trap. The trap includes a housing enclosing an interior chamber having a geometric extent of a given volumetric capacity. An inlet port is provided to open in fluid communication with the interior chamber and couplable to the inlet line. An outlet tube is provided to extend from a proximal end coupled to the outlet line to a distal end disposed within the housing to open in fluid communication with the interior chamber. Within the interior chamber, the first and second fluid are separated at an interface into a first and second fluid component according to the relative densities thereof. The outlet tube distal end is disposed within the chamber effective to define with respect to the interface a predetermined fill level of the second fluid maintaining the outlet line distal end within the second fluid component. This fill volume is substantially independent of the orientation of the trap within the fluid circuit. The second fluid stream is passed through the fluid circuit to accumulate at least a portion of the first fluid entrained therein within the trap.

The invention, accordingly, comprises the apparatus and method possessing the construction, combination of elements, and arrangement of parts and steps which are exemplified in the following detailed description. Reference to that description and to the accompanying drawings should be had for a fuller understanding and appreciation of the nature and objects of the invention, although other objects may be obvious to those skilled in the art.

BRIEF DESCRIPTION OF THE DRAWINGS

For a fuller understanding of the nature and objects of the invention, reference should be had to the following detailed description taken in connection with the accompanying drawings wherein.

The drawings will be described further in connection with the following Detailed Description of the Invention.

DETAILED DESCRIPTION OF THE INVENTION

The precepts of the position-independent fluid trap which is the subject of the present invention are described hereinafter in connection with its incorporation first into a hemodynamic or other parental liquid fluid circuit, and then in connection with its incorporation into a respiratory or other gaseous fluid circuit. However, it will be appreciated that the subject trap may find utility in other gaseous or liquid fluid circuits being connected intravenously, laryngeally, endotracheally, nasally, orally, or otherwise to a patient.

Figure 1:
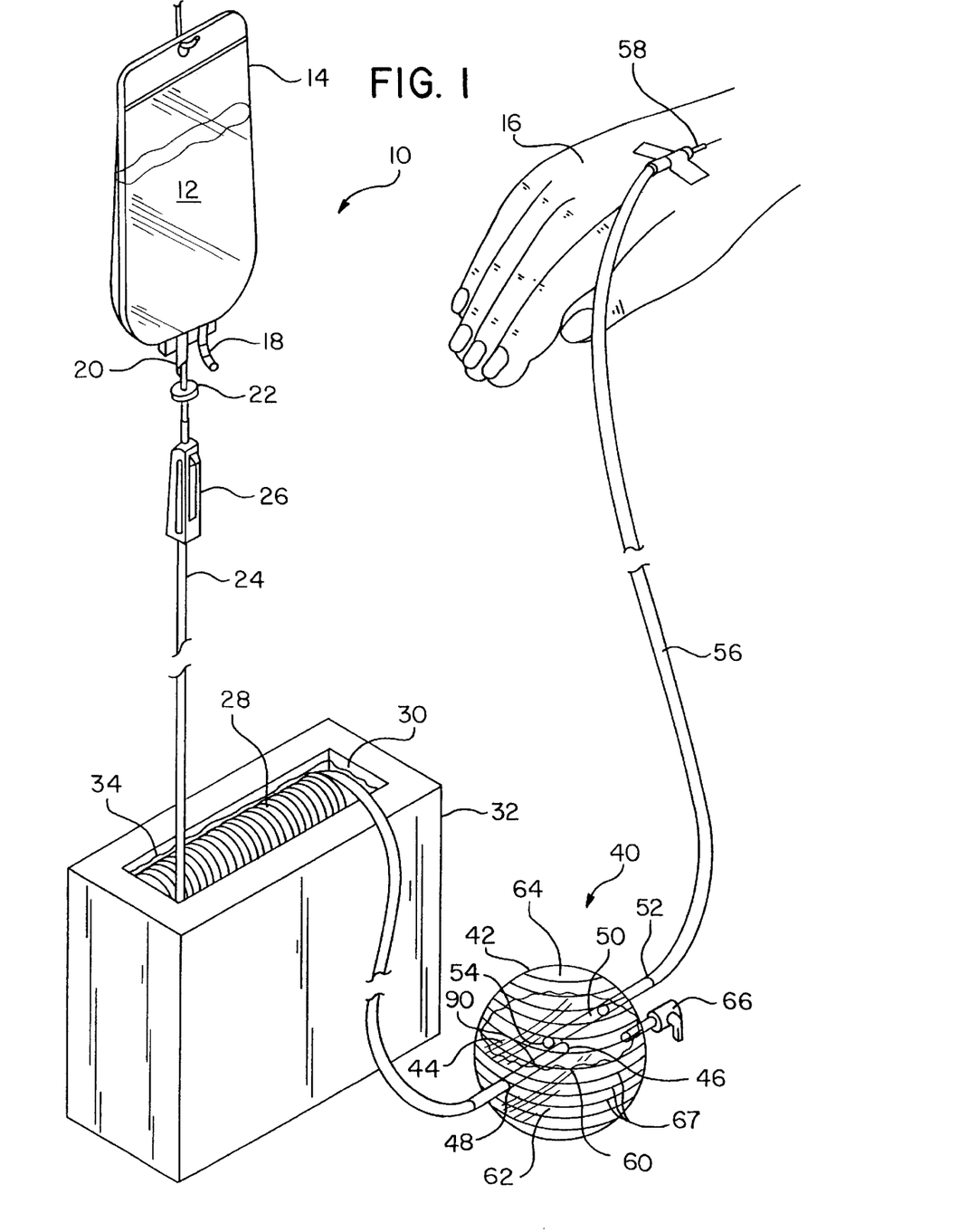
FIG. 1 is a perspective view of an exemplary hemodynamic fluid circuit as including one embodiment of the position-independent fluid trap of the present invention.

Referring then to the figures wherein like parts are designated with like reference numerals, shown generally at 10 in FIG. 1 is a hemodynamic circuit for infusing blood to a patient as modified to include the position-independent fluid trap of the present invention. Blood, 12, is shown to be contained in a disposable bag, 14, which is disposed at an elevated position with respect to the patient, shown at 16, for intravenous delivery thereto under hydrostatic pressure. Bag 14 typically is provided with one or more access ports, as are shown at 18 and 20, at least duplicate ports being provided for redundancy and to provide sites for the addition of a medicament or other parental fluid to the blood being administered. Port 20 is accessed by a needled connector, 22, coupling blood 12 in fluid communication with a first length of transparent tubing, 24. Tubing 24 may be received through a roll clamp, 26, which is actuable to meter the flow of blood from supply 12.

Tubing 24, which may have a length of 7 feet (2 m) or more, extends from connector 22 to a coiled, heat transfer portion shown at 28. Coil 28 is received within a reservoir, 30, of a blood warmer, 32, which for illustrative purposes is shown to be of a coiled tubing variety. In general operation, a heat transfer fluid, shown at 34, which is typically water or the like, is heated to a thermostaticly controlled temperature of about 37°–40° C. The blood or other fluid flowing through coil 28 is presented in a conductive heat transfer relationship with heat transfer fluid 34 and is warmed to a temperature of about 35°–40° C. Especially with blood as the transport fluid being administered, a significant outgassing of dissolved oxygen and carbon dioxide attends this warming resulting in the formation of air or gas bubbles which are entrained within the fluid flow stream. As aforementioned, these bubbles must be removed to avoid the infusion thereof to the patient 16 wherein a potentially fatal embolus could be developed. Tubing 24 therefore is coupled downstream of blood warmer to a fluid trap, 40, which is shown to be the position-independent fluid trap of the present invention. At startup, i.e., prior to the steady-state operation, trap 40 is filled with blood 12 for displacement as the outgas is accumulated.

In basic construction, trap 40, which may be disposable, includes a housing, 42, which preferably is transparent and formed of an polymeric material such as polyethylene, polypropylene, polyethylene terephthalate, or the like. Although shown for illustrative purposes as having a generally spherical geometry, other closed shapes, such as rectangular, square, cylindrical, elliptical, and the like, may be utilized for housing 42 and therefore are to be considered within the scope of the invention herein involved. Irrespective of the particular configuration selected, housing 42 defines an interior chamber, represented at 44, of a given volumetric capacity which may be about 25 cm$^3$, but which may be sized proportionately according to the constraints of the particular application.

An inlet port, 46, is provided to open in fluid communication with interior chamber 44, and is coupled to a terminal end, 48, of first length of tubing 24 which will be appreciated to define an inlet line of trap 40. In turn, an outlet tube, 50, is provided to extend from a proximal end, 52, to a distal end, 54, disposed within housing 42 to open in fluid communication with interior chamber 44. Proximal end 52 of outlet tube 50 is coupled to a second length of tubing, 56, which will be appreciated to define an outline line of trap 40. Tubing 56 extends from outlet tube 50 into intravenous fluid communication with patient 16 via a hypodermic needle, 58, which is shown to be subcutaneously disposed in the upper hand portion of patient 16.

As aforementioned, as the blood or other fluid being administered to patient 16 is warmed within warmer 32, the solubility coefficients of the gases dissolved therein are affected to an extent that significant outgassing occurs. As the warmed fluid flows into trap 40, at least a portion of the outgas is accumulated within interior chamber 44 thereof wherein a gas/liquid interface, represented at 60, is developed. For the specific circulatory application illustrated, interface 60 is defined, according to the relative densities of the first and second fluids within circuit 10, by a lower, liquid fluid component, shown at 62, and an upper, gaseous fluid component, shown at 64. At least one aspiration port, one of which is shown at 66, is provided for the aspiration of the gaseous component 64 for controlling the level of interface 60 determining the fluid fill level of trap 40. Although port 66 is shown for illustrative purposes to be a stopcock valve, it alternatively may be provided to be of a self-sealing variety accessible with a needle or syringe, or as capped port having, for example, a threaded LUER-LOK™ fitting connection. FIG. 1 also reveals that the outer surface of the trap 40 is configured having volume marking indicia 67 thereon. The indicia 67 resemble lattitudes and may be read by holding the trap 40 in the appropriate orientation wherein the liquid levels therein are parallel with the encircling lattitudes. Additionally, it may be found helpful to provide the interior surface of trap 40 with a non-sticking anti-coagulant surface. In this regard, the latter components will prevent or decrease the amount of clotted blood and/or secretions exhibiting an adhesive quality which may collect on the inside surface of trap 40. To provide such a feature, the inside of trap 40 may be bonded with Heparin, an acidic mucopolysaccharid composed of D-glucuronic acid and D-glucosamine. The surface also may be coated with a non-sticking substance such as Teflon®, a polytetrafluoroethylene substance.

Figure 2:
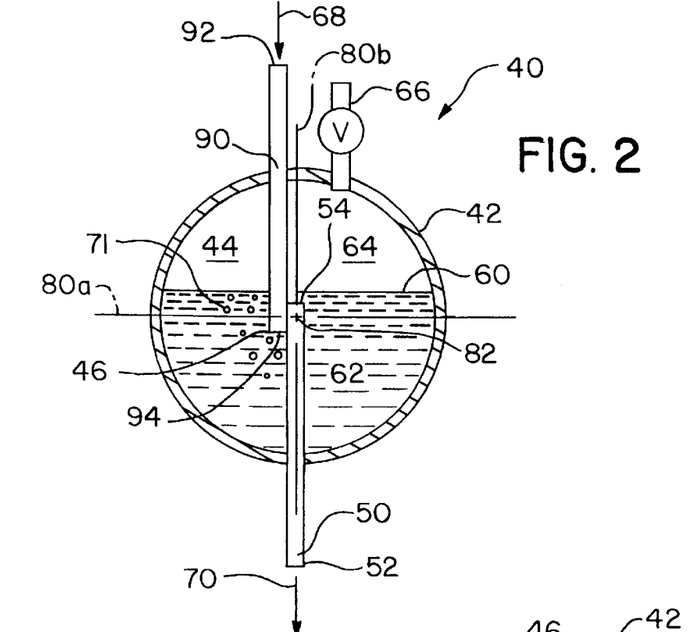
FIG. 2 is a cross-sectional view representative of the fluid trap of FIG. 1 illustrating the construction thereof in enhanced detail.

Referring next to FIG. 2, fluid trap 40 of the present invention is depicted in somewhat stylized sectional detail with the influent and effluent blood or other fluid streams thereof represented, respectively, by arrows 68 and 70, and with the outgassed air bubbles entrained in the fluid stream shown at 71. It will be appreciated that with outlet tube distal end 54 being disposed within housing 42 to open in fluid communication with interior chamber 44, a predetermined minimum fill volume of liquid fluid component 62 is defined which is substantially independent of the orientation of fluid trap 40 within the fluid circuit 10 of FIG. 1. That is, to the extent that distal end 54 of outlet tube 50 is maintained below the level of fluid interface 60, the blood or other liquid fluid stream being administered will flow through outlet tube 50 for infusion to patient 16 (FIG. 1).

Figures 3, 4, 5:
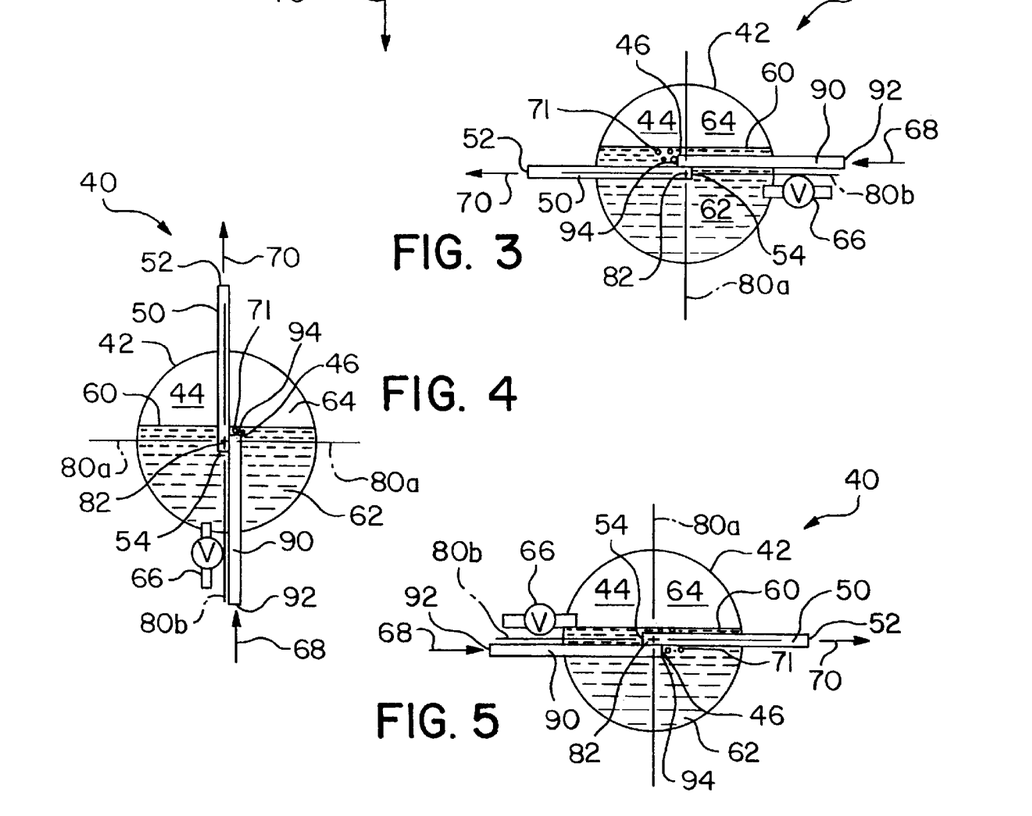
FIG. 3 is a schematic view of the fluid trap of FIG. 2 shown as disposed in a first orientation.
FIG. 4 is a schematic view of the fluid trap of FIG. 3 shown as disposed in a second orientation.
FIG. 5 is a schematic view of the fluid trap of FIG. 3 shown as disposed in a third orientation.

In this regard, reference with respect to FIG. 2 may be made to the sequence of FIGS. 3–4 wherein fluid trap 40 is schematically represented as disposed in various exemplary orientations. Specifically, trap 40 is shown in FIGS. 3–5 as having been rotated clockwise in successive 90° increments. It may be seen that, irrespective of the orientation of trap 40, outlet tube distal end 54 is operatively maintained within liquid fluid component 62 below the gravity-dependent level of interface 60. Liquid fluid component 62 therefore may be delivered through outlet tube 50 without regard, as was required for the fluid traps heretofore known in the art, to a generally vertical or otherwise normal orientation. Such a capability will be understood to be especially advantageous in fluid circuits such as illustrated in FIG. 1 which defy the positioning of the fluid trap in any one particular orientation.

Returning to FIG. 2, a preferred embodiment of trap 40 is shown wherein the geometric extent of interior chamber 44 is defined as being symmetrical about a pair of orthogonal central axes, shown at 80a and 80b, which intersect to define a geometric center or central locus or position, 82, at the volumetric center of interior chamber 44. For optimizing the predetermined minimum fill volume by maximizing the freeboard or headspace available for the accumulation of gaseous fluid component 64, outlet tube 50 is provided to extend within interior chamber 44 coaxially with one of central axes 80, with distal end 54 of tube 50 being disposed generally centrally within interior chamber 44. By "generally centrally," it is meant that outlet tube distal end 54 is located with respect to central locus 82 to define the predetermined minimum fill volume to be greater than about one half of the total volumetric capacity of interior chamber 44, and preferably no more than about 75% to 60% thereof. Accordingly, a minimum fill volume is defined which is greater than about one-half of the volumetric capacity of the interior chamber, but which, preferably, is no more than 75% to 60% thereof. Thus, depending upon the orientation of the trap, at least from about 25% to 40% of the volume is available for the accumulation of gaseous fluid 64. It will be appreciated that with the preferred disposition of distal end 54 of outlet tube 50, the minimum fill volume of interior chamber 44, as affected by the gravity-dependent fluid interface of the fluid components, is not substantially changed irrespective of the orientation of the trap. That is, whatever the orientation of the trap, about the same percentage of fill volume is above, for liquid flow streams, or below, for gaseous flow streams, the outlet port.

Trap 40 additionally includes an inlet tube, 90. Inlet tube 90 preferably is provided to extend generally parallel to outlet tube 50 from a first end, 92, couplable to outlet line 24 (FIG. 1), to a second end, 94, (FIG. 2) disposed within the housing 42 past outlet tube distal end 54 and opening in fluid communication with interior chamber 44 to define inlet port 46. Referring again to the sequence of FIGS. 3–4, it will be appreciated that with inlet tube 90 so provided, inlet port 46 is maintained at a generally consistent relationship with respect to interface 60 irrespective of the orientation of 40. Alternatively, however, for unidirectional flow streams of the type associated with the described circulatory circuit, inlet port 46 simply may be provided as a shortened tube or as another opening formed into housing 42.

Figure 6:
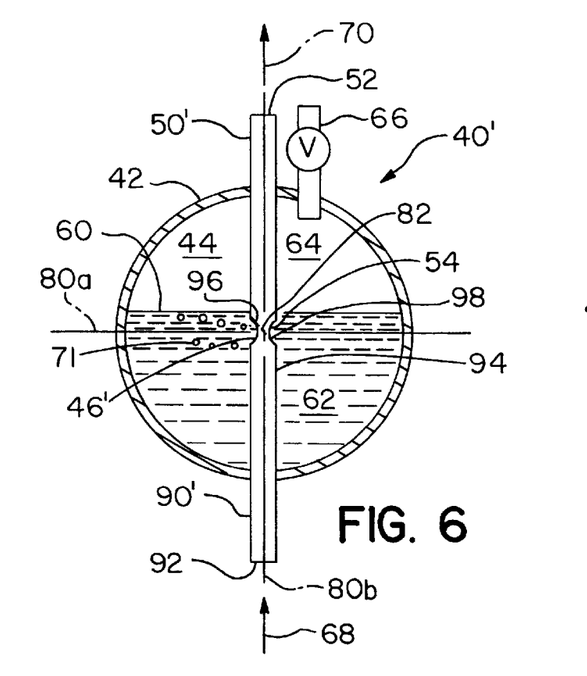
FIG. 6 is a cross-sectional view representative of another embodiment of the fluid trap of the present invention.
Figure 6A:
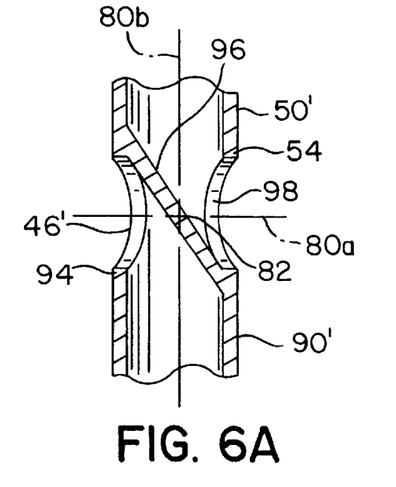
FIG. 6A is a cross-sectional view of the fluid trap of FIG. 6 showing the arrangement of the inlet and outlet tubes thereof in enhanced detail.

Referring next to FIG. 6, trap 40 of the present invention is depicted at 40' as configured with an alternative arrangement of inlet and outlet tubes, shown at 90' and 50'. Each of tubes 50' and 90' are provided to extend coaxially along an axis 80, with inlet tube 90 extending from first end 92 to second end 94. Again, second end 94 is disposed within housing 42 to open in fluid communication with interior chamber 44 for defining an inlet port, shown at 46'. Looking additionally to FIG. 6A, second end 94 of inlet tube 90' is shown to be coupled to distal end 54 of outlet tube 50', with an internal wall portion, 96, extending therebetween. Inlet port 46' is now formed as a generally circular aperture, with outlet tube distal end 54 likewise formed, as is shown at 98, as a generally circular aperture. Such an arrangement will be appreciated to locate both the distal end 54 of outlet tube 50' and the inlet port 46' of inlet tube 90' substantially at the central locus of axes 80 to thereby optimize both the minimum fill volume and headspace at about 50% of the volumetric capacity of interior chamber 44. Of course, other arrangements of inlet and outlet tubes, such as confronting but non-connected, orthogonal, and the like, will be obvious to those of ordinary skill in the art in view of the foregoing, and therefore are to be considered as within the precepts of the present invention.

Figure 7:
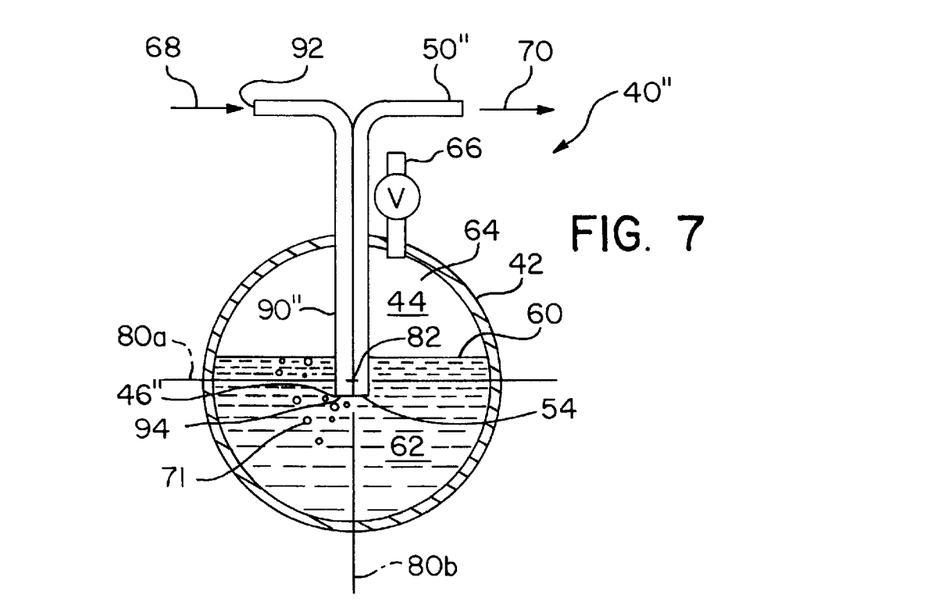
FIG. 7 is a cross-sectional view representative of another embodiment of the fluid trap of the present invention.

Referring to FIG. 7, trap 40 of the present invention is depicted at 40" as configured with another arrangement of inlet and outlet tubes as shown, respectively, at 90" and 50". Each of the tubes 90" and 50" are arranged to extend along an axis 80, herein identified as 80b in an abutting, mutually parallel arrangement. Thus, inlet port 46" of the inlet tube 90" is positioned in immediate coplanar adjacency with distal end 54 of outlet tube 50". Such an arrangement may be preferred by manufacturers as promoting a more facile assembly.

Figure 8:
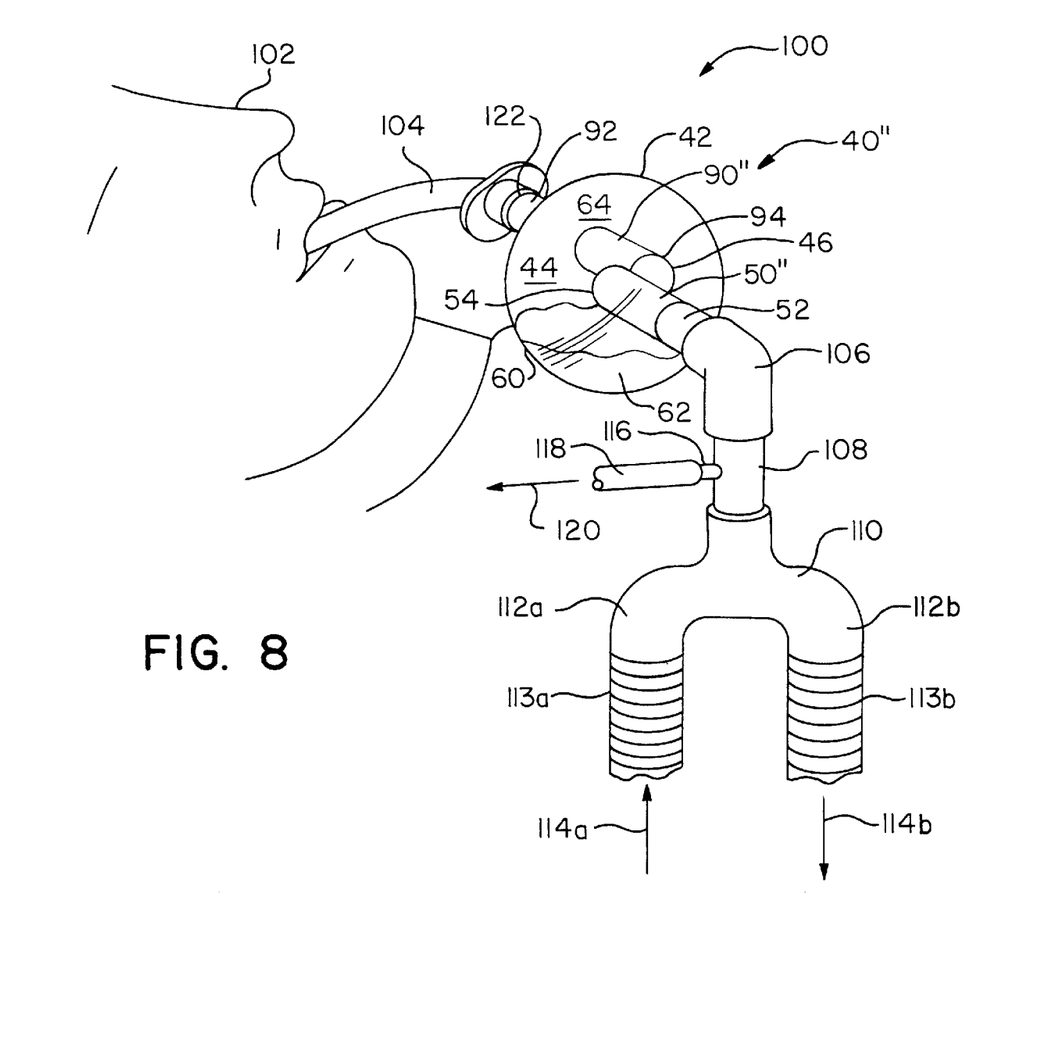
FIG. 8 is a perspective view showing an endotracheal fluid circuit as including yet another embodiment of the position-independent fluid trap of the present invention.

Turning next to FIG. 8, yet another alternative embodiment of fluid trap 40 of the present invention is shown at 40'" as incorporated into a breathing circuit for the respiratory management of a ventilator patient, 102. Patient 102 is shown as having been intubated with an endotracheal (ET) tube, 104, which is connected to inlet tube 90'" of trap 40'". Outlet tube 50'" of trap 40'", in turn, is connected in fluid communication via a right angle connector, 106, and an airway adapter, 108, to a Y-connector, 110, which branches to an inspiratory limb, 112a, and an expiratory limb, 112b. Each of limbs 112 is connected by a length of corrugated tubing, 113a and 113b, to a ventilator which establishes through circuit 100, as is represented by arrows 114a and 114b, a fluid flow delivering inspiratory gases to and removing expiratory gases from patient 102. Airway adapter 108 is optionally provided and includes a sampling port, 116, coupled via tubing 118 to provide the gas flow represented by arrow 120 to a gas monitor or analyzer (not shown), which may be employed to measure the composition of the inspiratory or expiratory gases of patient 102. Although ET tube 104 is shown as being orally received by patient 102, for the purposes of the present discussion, a nasal or tracheostomic insertion is to be considered equivalent. Alternatively, a laryngeal mask airway or face mask assembly may be substituted for ET tube 104.

The inspired air being delivered to patient 102 through limb 114a typically has been heated and humidified and, consequently, may develop condensation in the tubing circuitry. Water vapor, mucous, and other secretions from patient 102 also may collect in ET tube 104 and restrict the fluid flow therethrough. Liquid or condensate from either source, apart from requiring periodic suctioning from the circuit to avoid ingress into the lungs of patient 102, additionally presents a risk of permanent damage to any gas analyzer or monitor being utilized if passed thereto via sampling port 116. Accordingly, fluid trap 40'" is interposed between ET tube 104 and airway adapter 108 to collect at least a portion of the liquid entrained in the gas streams flowing through circuit 100, which liquid is accumulated within interior chamber 44 as liquid component 62. Alternatively, if no airway adapter 108 is provided, trap 40'" may be interposed between ET tube 104 and connector 106 or 110.

In basic construction, trap 40'" includes a housing, 42, which preferably is transparent and formed of an polymeric material such as polyethylene, polypropylene, polyethylene terephthalate, or the like. Shown again for illustrative purposes as having a generally spherical geometry, housing 42 alternatively may be configured as having a rectangular, square, cylindrical, elliptical, or other closed geometry. Irrespective of the particular configuration selected, housing 42 defines interior chamber 44 of a given volumetric capacity which may be about 50 cm$^3$. However, as such capacity represents a deadspace in circuit 100, the volume thereof may be sized accordingly to accommodate pediatric and neonatal patients, for example, having relatively lower tidal volumes.

As before, inlet port 46 is provided to open in fluid communication with interior chamber 44, and is coupled to a terminal end connector end, 122, of ET tube 104. In turn, outlet tube 50''' is provided to extend from proximal end 52 coupled to right angle connector 106, to distal end 54 disposed within housing 42 to open in fluid communication with interior chamber 44. ET tube 104 and right angle connect 106 will be understood to correspond, respectively, to the first and second lengths of tubing 24 and 56 discussed previously in connection with FIG. 1.

Figure 9:
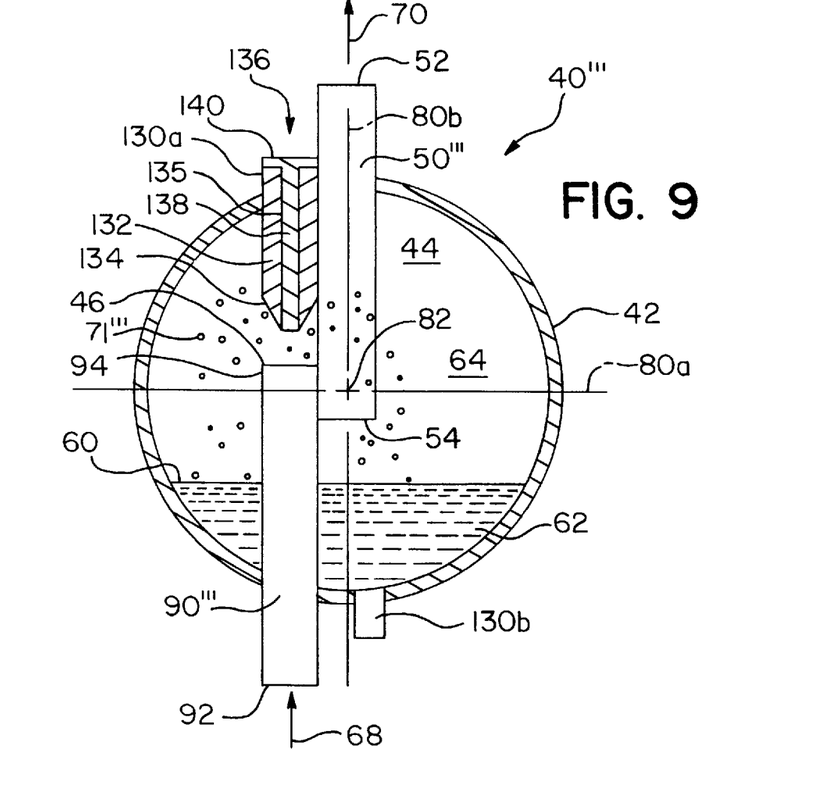
FIG. 9 is a cross-sectional-view of representative of the fluid trap of FIG. 8 illustrating the construction thereof in enhanced detail.

Referring next to FIG. 9, a preferred embodiment of fluid trap 40''' of the present invention is depicted in somewhat stylized sectional detail with the influent and effluent gas stream thereof represented, respectively, by arrows 68 and 70, and with the liquid entrained in the gas stream shown at 71'''. A gas/liquid interface 60 is defined according to the relative densities of the first and second fluids within the fluid circuit. For the specific respiratory application illustrated, that interface, again, is defined by lower liquid fluid component 62 and upper gaseous component 64. With outlet tube distal end 54 being disposed within housing 42 to open in fluid communication with interior chamber 44, a predetermined minimum fill volume of gaseous fluid component 64 now is defined which is substantially independent of the orientation of fluid trap 40''' within the fluid circuit 100 of FIG. 8. That is, to the extent that distal end 54 of outlet tube 50''' is maintained above the level of fluid interface 60, the expiratory gas stream from patient 102 entering device 42 from inlet tube 90''' will flow through outlet tube 50''' to sampling port 116 and expiratory limb 114b of circuit 100 (FIG. 8).

As before, the geometric extent of interior chamber 44 is defined as being symmetrical about orthogonal central axes 80, which intersect to define geometric center or central locus 82. For optimizing the predetermined minimum fill volume by maximizing the freeboard space available for the accumulation of liquid fluid component 62, outlet tube 50'' is provided to extend within interior chamber 44 coaxially with one of central axes 80, with distal end 54 of tube 50'' again being disposed "generally centrally" within interior chamber 44. Accordingly, a minimum fill volume is defined which is greater than about one half of the total volumetric capacity of the interior chamber, but which preferably is no more than from about 75% to 60% thereof such that, depending upon the orientation of the trap, at least from about 25% to 40% is available for the accumulation of liquid fluid 62.

Inlet tube 90''' preferably is provided to extend generally parallel to outlet tube 50''' from first end 92 couplable to ET tube 104 (FIG. 8), to second end 94 disposed within housing 42 past outlet tube distal end 54 and opening in fluid communication with interior chamber 44 to define inlet port 46. It will be appreciated that with inlet tube 90'' so provided, inlet port 46 is maintained at a generally consistent relationship with respect to interface 60 irrespective of the orientation of trap 40'''.

Thus, as compared to inlet and outlet tubes 90 and 50 of trap 40, tubes 90'' and 50'' of trap 40'' are functionally identical and are shown to differ in structure, essentially, only as being sized with a larger internal diameter to accommodate the volumetric flow of gas through circuit 100. However, as the gas flow through circuit 100 is reversed during the inspiratory and expiratory cycles of the ventilator, it will be appreciated that the condensate, secretions, mucous, and like liquids occurring in circuit 100 may enter trap 40''' via either inlet tube 90''' or outlet tube 50''' thereof. In this regard, the disposition of inlet and outlet tubes 90'' and 50''' in the described arrangement additionally is preferred for bidirectional fluid flow circuits as affording a positioning independence for trap 40'' during, for example, both the aforementioned inspiratory and expiratory cycles.

At least one aspiration or drain port, a pair of which are now shown at 130a and 130b, is provided for the removal with a suction catheter, syringe, or the like of the liquid component 62 from interior chamber 44 for controlling the level of interface 60 therein to be below outlet tube distal end 54. Alternatively, a low-flow rate suction pump (not shown) may be attached to one or more of the ports 130 for the continuous removal of the liquid component 62. Indeed, with six or more geometrically spaced ports 130 and a corresponding number of suction pumps, a position-independent system may be envisioned for the continuous removal of the liquid component 62. Ports 130 additionally may be accessed for the withdrawal of mucous samples for culturing, and may be provided for connection to a closed suction system such as that disclosed in U.S. Pat. Nos. 3,991,762; 4,569,344; 4,696,296; and 4,836,199.

Figure 10:
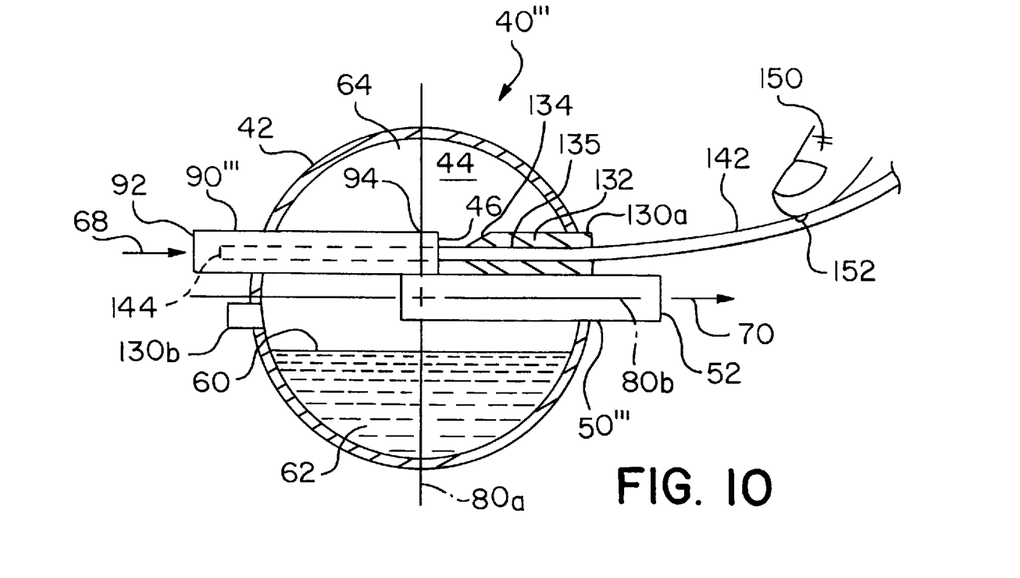
FIG. 10 is a cross-sectional view corresponding with that shown in FIG. 9 and illustrating the insertion of a suction catheter through the fluid trap.

Returning, in particular, to the port 130a, it may be observed that it is configured to provide an angle deflection arrangement to promote a transverse or sideways deflection or movement of secretions which the patient may cough up. Thus, the port 130a is configured as an outer cylinder 132 which extends to a truncated conical tip 134 which is aligned with the central axis of inlet tube 90'''. Cylindrical component 132 is provided with a centrally disposed cylindrically shaped passageway 135 passing therethrough which is normally blocked by a removable obturator 136. Obturator 136 is shaped generally as a blunt, headed nail having a cylindrical shaft component 138 surmounted by a cap 140. In addition to the desirable deflection of expectorant or other effluvia emanating from the patient, the ET tube may be accessed with a suction catheter. Looking additionally to FIG. 10, the obturator 136 is shown having been removed from outer cylinder 132 and a suction catheter 142 having a tip 144 is seen to have been inserted through centrally disposed opening 135. In conventional fashion, control over the application of suction is by finger pressure such as represented at 150 over a small port 152 in the suction catheter. Such catheters as at 142 typically are connected to a suction source such as a wall suction outlet or portable suction machine conventionally found in the clinical environment. The embodiment shown is referred to as an "open suction" system in contrast to the "closed suction" systems where patient circuit air cannot freely escape into the ambient surroundings, but can only be removed through the catheter.

As it is anticipated that certain changes may be made in the present invention without departing from the precepts herein involved, it is intended that all matter contained in the foregoing description shall be interpreted as illustrative and not in a limiting sense. All references cited herein are expressly incorporated by reference.

What is claimed:

1. A fluid trap for separating at least a portion of a first fluid of a first density entrained within a flow stream of a second fluid stream of a second density flowing through a fluid circuit, said trap being connectable within a fluid circuit and including a first conduit defining an inlet line of said trap and to a second conduit defining an outlet line of said trap and comprising:

a housing enclosing an interior chamber having a geometric extent of a given volumetric capacity;

an inlet port opening in fluid communication with said interior chamber and couplable to said inlet line; and an outlet tube extending from a proximal end couplable to said outlet line to a distal end disposed within said housing and opening in fluid communication with said interior chamber, first and second fluids being separated at an interface within said interior chamber into a first and a second fluid component according to their relative densities, and said outlet tube distal end being disposed within said interior chamber effective to define with respect to said interface a predetermined fill volume of a second fluid maintaining said outlet tube distal end within a second fluid component, said predetermined fill volume being substantially independent of the orientation of said fluid trap within a fluid circuit.

2. The fluid trap of claim 1 wherein said predetermined fill volume is greater than about one half of said volumetric capacity of said interior chamber.

3. The fluid trap of claim 1 wherein said geometric extent of said interior chamber is defined as being symmetrical about a pair of orthogonal central axes.

4. The fluid trap of claim 3 wherein said outlet tube extends within said interior chamber coaxially with one of said central axes.

5. The fluid trap of claim 4 wherein said outlet tube distal end is disposed generally centrally within said interior chamber.

6. The fluid trap of claim 1 further comprising an inlet tube extending generally parallel to said outlet tube from a first end couplable to said inlet line, to a second end disposed within said housing past said outlet tube distal end and opening in fluid communication with said interior chamber to define said inlet port.

7. The fluid trap of claim 1 wherein said interior chamber has a generally spherical geometric extent.

8. The fluid trap of claim 1 further comprising at least one aspiration port openable in fluid communication with said interior chamber for removing a first fluid therefrom.

9. The fluid trap of claim 1 wherein said inlet line extends from said inlet port of said fluid trap into fluid communication with a heat exchanger, and said outlet line extends from said outlet tube into intravenous fluid communication with a patient.

10. The fluid trap of claim 1 wherein said inlet line extends from said inlet port of said fluid trap into tracheal fluid communication with a patient, and said outlet line extends into fluid communication with a ventilator.

11. The fluid trap of claim 1 wherein said interior chamber has a volumetric capacity of about from about 25 cm$^3$ to about 50 cm$^3$.

12. The fluid trap of claim 1 further comprising an inlet tube extending from a first end couplable to said inlet line to a second end disposed within said housing and opening in fluid communication with said interior chamber to define said inlet port.

13. The fluid trap of claim 12 wherein said second end of said inlet tube is coupled to said distal end of said outlet tube.

14. The fluid trap of claim 1 wherein:

said inlet line extends from said inlet port of said fluid trap into tracheal fluid communication with a patient;

said outlet line extends into fluid communication with a ventilator;

further comprising:

an inlet tube extending from a first end couplable to said inlet line, to a second end disposed within said housing past said outlet tube distal end and opening in fluid communication with said interior chamber to define said inlet port;

an aspiration port mounted upon said housing and including a passageway extending from an access port located externally of said housing to an outlet positioned in confronting relationship with said outlet tube distal end, said passageway having a cross-sectional extent effective for slideably receiving a suction catheter, and including an obturator removably positionable within said passageway for blocking it.

15. The fluid trap of claim 14 in which said aspiration port is configured at said passageway outlet as a deflector effective to laterally deflect patient generated fluids exiting said inlet tube second end.

16. The fluid trap of claim 1 further comprising an inlet tube extending generally parallel to and in adjacency with said outlet tube from a first end couplable to said inlet line, to a second end within said housing conterminus with said outlet tube distal end and opening in fluid communication with said interior chamber to define said inlet port.

17. A method within a fluid circuit for separating at least a portion of a first fluid of a first density entrained within a flow stream of a second fluid of a second density comprising the steps of:

(a) providing a fluid trap connected within a fluid circuit to a first conduit defining an inlet line of said trap and to a second conduit defining an outlet line of said trap, said trap comprising:

a housing enclosing an interior chamber having a geometric extent of a given volumetric capacity;

an inlet port opening in fluid communication with said interior chamber and couplable to said inlet line; and an outlet tube extending from a proximal end coupled to said outlet line to a distal end disposed within said housing and opening in fluid communication with said interior chamber, a first and a second fluid being separated at an interface within said interior chamber into a first and a second fluid component according to their relative densities, and said outlet line distal end being disposed within said interior chamber effective to define with respect to said interface a predetermined fill volume of said second fluid maintaining said outlet line distal end within a second fluid component, said fill volume being substantially independent of the orientation of said fluid trap within said fluid circuit; and (b) flowing a second fluid stream through such as fluid circuit to accumulate at least a portion of a first fluid entrained therein within said trap.

18. The method of claim 17 wherein said fill volume is provided as being greater than about one half of said volumetric capacity of said interior chamber.

19. The method of claim 17 wherein said geometric extent of said interior chamber is provided as being symmetrical about a pair of orthogonal central axes.

20. The method claim 19 wherein said outlet tube is provided to extend within said interior chamber coaxially with one of said central axes.

21. The method of claim 20 wherein said outlet tube is disposed generally centrally within said interior chamber.

22. The method of claim 17 wherein said fluid trap is provided as further comprising an inlet tube extending generally parallel to said outlet tube from a first end couplable to said inlet line, to a second end disposed within said housing past said outlet tube distal end and opening in fluid communication with said interior chamber to define said inlet port.

23. The method of claim 17 wherein said interior chamber of said fluid trap is provided as having a generally spherical geometric extent.

24. The method of claim 17 wherein said fluid trap is provided as further comprising at least one aspiration port openable in fluid communication with said interior chamber for removing a first fluid therefrom, and further comprising the step:

(c) aspirating a first fluid through said aspiration port to maintain such as first fluid accumulated within said interior chamber below said predetermined fill level.

25. The method of claim 17 wherein said inlet line is provided to extend from said inlet port of said fluid trap into fluid communication with a heat exchanger, and said outlet line is provided to extend from said outlet tube into intravenous fluid communication with a patient.

26. The method of claim 17 wherein said inlet line is provided to extend from said inlet port of said fluid trap into tracheal fluid communication with a patient, and said outlet line is provided to extend into fluid communication with a ventilator.

27. The method of claim 17 wherein said interior chamber of said fluid trap is provided as having a volumetric capacity of from about 25 cm$^3$ to about 50 cm$^3$.

28. The method of claim 17 wherein said fluid trap is provided as further comprising an inlet tube extending from a first end couplable to said inlet line to a second end disposed within said housing and opening in fluid communication with said interior chamber to define said inlet port.

29. The method of claim 28 wherein said second end of said inlet tube is provided as being coupled to said distal end of said outlet tube.

30. The method of claim 17 wherein said fluid trap is provided as further comprising an inlet tube extending from a first end coupled to said first end of said outlet tube within said housing to a second end couplable to said inlet line, said inlet tube having at least one aperture formed thereinto and disposed within said interior chamber defining said inlet port.

31. The method of claim 17 wherein a first fluid comprises a liquid and a second fluid comprises a gas.

32. The method of claim 17 wherein a first fluid comprises a gas and a second fluid comprises a liquid.

33. The method of claim 17 wherein a fluid circuit is an extracorporeal fluid circuit of a patient.

34. The method of claim 17 wherein a fluid circuit is in a breathing circuit of a patient.

* * * * *